United States Patent
Feng et al.

(10) Patent No.: US 9,884,799 B2
(45) Date of Patent: Feb. 6, 2018

(54) SURFACTANT COMPOSITION COMPRISING ETHER COMPOUND AND CATALYTIC PROCESS FOR MANUFACTURING THEREOF

(71) Applicants: RHODIA OPERATIONS, Paris (FR); Centre National De La Recherche Scientifique, Paris (FR)

(72) Inventors: Xiaoshuang Feng, Shanghai (CN); Floryan Decampo, Shanghai (CN); Yan Zhao, Shanghai (CN); Zhaoyu Fan, Shanghai (CN); Luca Merlo, Montorfano (IT); Claudio Oldani, Nerviano (IT)

(73) Assignees: Rhodia Operations, Paris (FR); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 15/027,645

(22) PCT Filed: Oct. 7, 2014

(86) PCT No.: PCT/CN2014/088110
§ 371 (c)(1),
(2) Date: Apr. 6, 2016

(87) PCT Pub. No.: WO2015/051733
PCT Pub. Date: Apr. 16, 2015

(65) Prior Publication Data
US 2016/0251290 A1 Sep. 1, 2016

(30) Foreign Application Priority Data

Oct. 11, 2013 (WO) ................ PCT/CN2013/085018
Apr. 1, 2014 (WO) ................ PCT/CN2014/074471

(51) Int. Cl.
| | | |
|---|---|---|
| C07C 41/00 | (2006.01) | |
| C08G 65/00 | (2006.01) | |
| B01J 31/00 | (2006.01) | |
| C11D 1/00 | (2006.01) | |
| C07C 41/09 | (2006.01) | |
| C08G 65/34 | (2006.01) | |
| B01J 31/10 | (2006.01) | |
| C11D 1/72 | (2006.01) | |
| C08L 71/00 | (2006.01) | |

(52) U.S. Cl.
CPC .............. *C07C 41/09* (2013.01); *B01J 31/10* (2013.01); *C08G 65/34* (2013.01); *C08L 71/00* (2013.01); *C11D 1/72* (2013.01); *C08G 2650/54* (2013.01)

(58) Field of Classification Search
CPC .......... C07C 41/09; B01J 31/10; C08G 65/34; C08L 71/00; C11D 1/72
See application file for complete search history.

(56) References Cited

U.S. PATENT DOCUMENTS

| | | |
|---|---|---|
| 4,833,060 A | 5/1989 | Nair et al. |
| 2005/0156340 A1 | 7/2005 | Valianatos et al. |
| 2007/0238905 A1* | 10/2007 | Arredondo .............. C07C 41/09 568/672 |
| 2010/0029799 A1 | 2/2010 | Miyata et al. |

FOREIGN PATENT DOCUMENTS

| | | |
|---|---|---|
| EP | 1958929 A1 | 8/2008 |
| WO | WO 2007092407 A2 | 8/2007 |
| WO | WO 2012082157 A2 | 6/2012 |

OTHER PUBLICATIONS

Weckhuysen et al.—Chemical Imaging of Catalyst Deactivation during the Conversion of Renewables at the Single Particle Level: Etherification of Biomass-Based Polyols with Alkenes over H-Beta Zeolites (2010) J. Amer. Chem. Soc. vol. 132, p. 10429-10439 (11 pages).
Weckhuysen et al.—Synthesis of long alkyl chain ethers through direct etherification of biomass-based alcohols with 1-octene over heterogeneous acid catalysts (2009) J. Catal. 2009, vol. 268, 251-259 (9 pages).
Lemaire et al.—Selective synthesis of 1-O alkyl glycerol and diglycerol ethers by reductive alkylation of alcohols (2010) Green Chem. vol. 12, 2189-2195 (7 pages).
Sutter et al.—1-O-Alkyl (di)glycerol ethers synthesis from methyl esters and triglycerides by two pathways: catalytic reductive alkylation and transesterification/reduction (2013) Green Chem, 15, 786-797 (12 pages).

* cited by examiner

*Primary Examiner* — Sikarl Witherspoon
(74) *Attorney, Agent, or Firm* — Jarrod N. Raphael

(57) ABSTRACT

Disclosed is a process for preparing at least one ether compound, comprising reacting at least one alcohol (I) with at least one polyol (II) in the presence of a functional polymer [polymer (F)] as a catalyst (X), wherein: the alcohol (I) is represented by the general formula (1): R1-OH (1) wherein R1 is a hydrocarbon group having 1 to 36 carbon atoms, the polyol (II) is represented by the general formula (2): R2-(OH) m (2) wherein R2 represents the skeleton moiety of the polyol and m is an integer of from 2 to 20, and polymer (F) is a polymer comprising recurring units derived from at least one ethylenically unsaturated monomer [monomer (M)] and bearing at least one cation exchange group. Further disclosed is a surfactant composition obtained by said process, and featuring an excellent detergency performance.

17 Claims, No Drawings

SURFACTANT COMPOSITION COMPRISING ETHER COMPOUND AND CATALYTIC PROCESS FOR MANUFACTURING THEREOF

CROSS-REFERENCE TO RELATED APPLICATIONS

The present application is a U.S. national phase entry under 35 U.S.C. § 371 of International Application No. PCT/CN2014/088110, filed on Oct. 7, 2014, which claims priority to International Application Nos. PCT/CN2013/085018 filed on 11 Oct. 2013 and PCT/CN2014/074471 filed on 1 Apr. 2014, the whole content of these applications being incorporated herein by reference. Should the disclosure of any patents, patent applications, and publications which are incorporated herein by reference conflict with the description of the present application to the extent that it may render a term unclear, the present description shall take precedence.

TECHNICAL FIELD

The present invention concerns a surfactant composition comprising at least one ether compound, and a catalytic process for manufacturing the same by reacting at least one alcohol with at least one polyol.

BACKGROUND ART

In recent years, the increasing demand of biodiesel as a renewable energy resource has led to an overproduction of glycerol-based compounds, which are inevitable by-products of the trans-esterification process for producing biodiesel. Unfortunately, the abundant glycerol-based compounds thus produced not only increased storage burden for the biodiesel producer, but also posed an environmental pollution risk. Therefore, new and efficient industrial processes are eagerly searched to efficiently transform the surplus glycerol-based compounds into higher value-added chemicals.

In this aspect, it has been conventionally known to convert glycerol-based compounds to (poly)glyceryl ethers and their derivatives which, due to their amphiphilic nature and other chemical properties, are used in many industrial applications such as solvents, emulsifiers, laundry and cleaning formulations, dispersants, foaming agents, and ink formulations. Said conversion is usually fulfilled through an etherification reaction of a glycerol-based compound or its derivative, in which hydrophilic glyceryl moieties is incorporated onto a long alkyl chain provided by a hydrophobic alcohol. Traditionally, said etherification is realized by Williamson ether synthesis, which uses toxic and expensive glycerol derivatives (epichlorohydrin, 3-chloropropane-1,2-diol or glycidol) as starting materials and needs a strong base to reach a reasonably selectivity.

As an alternative route of etherification, EP 1958929 A (KAO CORPORATION) Dec. 7, 2006 described a process for producing polyglyceryl ether surfactants, which comprises reacting an alcohol with a glycidol in the presence of a simple metal salt of rare earth element as catalyst. While this process appears to produce a moderate-to-high conversion rate of the alcohol reactant, such is not a direct etherification of glycerol with alkyl alcohol, but rather etherification of glycidol compounds. Compared to glycerol, glycidol compounds are more difficult and expensive to manufacture, and also have an adverse tendency of self-polymerization.

Despite the obvious limitations of indirect (poly)glycerol etherification, using direct etherification of (poly)glycerol compounds to prepare ether has been challenging. This is partly caused by the high viscosity and hydrophilic nature of these glycerol-based compounds, which hinders their interaction with a hydrophobic substrate such as an alkyl alcohol in a chemical reaction. Moreover, since glycerol has three hydroxyl groups with similar pKa, with the presence of hydroxyl groups in the ether product, the selectivity control is made even more complicated.

In the previous research work of this field, Wechhuysen, et al reported direct etherification reaction of biomass-based polyols with long-chain olefins under heterogeneous acidic catalysis, in which good results were obtained for diols. However, very low conversion (~20%) was given in the case of glycerol, see WECKHUYSEN, et al. Chemical Imaging of Catalyst Deactivation during the Conversion of Renewables at the Single Particle Level: Etherification of Biomass-Based Polyols with Alkenes over H-Beta Zeolites. *J. Amer. Chem. Soc.* 2010, vol. 132, p. 10429-10439. and WECKHUYSEN, et al. Synthesis of long alkyl chain ethers through direct etherification of biomass-based alcohols with 1-octene over heterogeneous acid catalysts. *J. Catal.* 2009, vol. 268, p. 251-259.

Lemaire, et al studied an alternative route to etherify glycerol and obtain 1-O-alkyl glycerol and diglycerol ethers, by catalytic reductive alkylation of glycerol and diglycerol with linear aldehydes in the presence of 0.5 mol % of Pd/C under 10 bars of hydrogen using a Brønsted acid as co-catalyst. See LEMAIRE, et al. Selective synthesis of 1-O-alkyl glycerol and diglycerol ethers by reductive alkylation of alcohols. *Green Chem.* 2010, vol. 12, p. 2189-2195. More recently, the same research group reported the realization of a reductive alkylation of (di)glycerol with bio-sourced fatty acid methyl esters, under an even more stringent reaction condition: 50 bar hydrogen pressure in the presence of 1 mol % of Pd/C and an acid co-catalyst. See LEMAIRE, et al. 1-O-Alkyl (di)glycerol ethers synthesis from methyl esters and triglycerides by two pathways: catalytic reductive alkylation and transesterification/reduction. *Green Chem.* 2013, vol. 15, p. 786-797.

From our previous work (PCT/CN2012/078114), we have found that it is possible to produce glyceryl ether compounds by a direct etherification of glycerol with alkyl alcohol, using a specific Pickering emulsion condition (emulsion stabilized by solid nanoparticles) and optionally with an acidic catalyst. While this newly discovered process advantageously avoids the need of stringent reaction condition (e.g. high pressure or expensive catalyst) and conveniently uses the inexpensive glycerol compounds as starting material, there is still room to improve its reactant conversion rate and product selectivity. Moreover, when a liquid acid catalyst is used in the etherification reaction, extra recycling steps involving liquid-liquid separation would inevitably increase the production cost.

As such, there remains a need to develop a novel process for realizing a direct etherification of glycerol based compounds with alkyl alcohol, which features a higher reactant conversion rate, product selectivity, mild reaction condition and easy recycling of catalysts.

SUMMARY OF INVENTION

In one aspect, the present invention is directed to a process for preparing at least one ether compound, comprising reacting at least one alcohol (I) with at least one polyol (II) in the presence of a functional polymer [polymer (F)] as a catalyst (X), wherein:
the alcohol (I) is a compound represented by the general formula (1):

$R_1$—OH  (1)

wherein $R_1$ is a hydrocarbon group having 1 to 36 carbon atoms, the polyol (II) is represented by the general formula (2):

$R_2$—(OH)$_m$  (2)

wherein $R_2$ represents the skeleton moiety of the polyol and m is an integer of from 2 to 20,
and the polymer (F) is a polymer comprising recurring units derived from at least one ethylenically unsaturated monomer [monomer (M)] and bearing at least one cation exchange group.

As the Applicant has surprisingly found out, the aforementioned etherification process not only gives a satisfactory reactant conversion rate, but also provides an ether product with high surfactant activity for a wide range of industrial applications. Moreover, the above etherification process also avoids the usage of expensive/toxic reagents as well as harsh reaction condition, and is advantageously realized via a catalyst (X) that is easy to recycle: after repeated use and with no apparent activity loss.

In another aspect of the invention, it is directed to a product susceptible to be obtained by the etherification process as afore-described, or a surfactant composition characterized by including:
(i) more than one ether compound of formula (3) [ether (E1)],

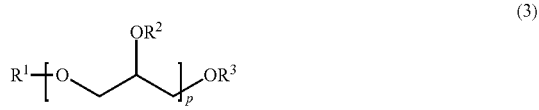

wherein: p is an integer from 1 to 36, and radicals $R^1$, $R^2$, and $R^3$, being same or different, are independently a hydrogen atom or a hydrocarbon group having 1 to 36 carbon atoms and optionally containing oxygen atom, provided that $R^2$ and $R^3$ are not hydrogen at the same time, and wherein $R^2$ optionally join together with $R^1$ or $R^3$ to form at least one oxygen-containing cyclic group having 3 to 7 carbon atoms;
(ii) at least one polyol (II) compound represented by the general formula (2):

$R_2$—(OH)$_m$  (2)

wherein $R_2$ represents the skeleton moiety of the polyol and m is an integer of from 2 to 20; and,
(ii) optionally, at least one mono alkyl glyceryl ether (MAGE) compound of formula (4):

wherein a is an integer of from 1 to 20, and radical $R_1$ is a hydrocarbon group having 1 to 36 carbon atoms, as defined above.

For the purpose of the invention, the term "hydrocarbon group" is used herein in a broad sense to mean an alkyl, aryl, aralkyl, alkaryl, alkenyl, or alkoxyl radical, optionally fluorinated, and optionally comprising elements other than carbon and hydrogen such as oxygen, nitrogen, sulphur and silicon.

"Alkyl" as used herein means a straight chain or branched saturated aliphatic hydrocarbon residue. "Aryl" as used herein means a 6-carbon monocyclic or 10-carbon bicyclic aromatic ring system wherein 0, 1, 2, 3, or 4 atoms of each ring are optionally substituted. Examples of aryl groups include phenyl, naphthyl and the like. The term "arylalkyl" or the term "aralkyl" refers to alkyl substituted with an aryl, and the term "alkaryl" as used herein refers to aryl substituted with an alkyl. As used herein, "alkenyl" refers to a straight chain or branched aliphatic hydrocarbon residue having at least one carbon-carbon double bond, and "alkoxyl" refers to the group "alkyl-O—", wherein alkyl is as defined above.

As previously defined, the alcohol (I) is a compound represented by the general formula (1):

$R_1$—OH  (1)

wherein $R_1$ is a hydrocarbon group having 1 to 36 carbon atoms.

The alcohol (I) may notably be a hydrophobic alcohol. For the purpose of the invention, a "hydrophobic" molecule or portion of a molecule is one that is repelled from a mass of water and other polar substances, and a "hydrophilic" molecule or portion of a molecule is one that has a tendency to interact with or be dissolved by water and other polar substances.

Hydrophobic nature of the alcohol (I) is usually provided by the hydrophobic portion of hydrocarbon group $R_1$, such as alkylated groups or alkoxylated groups. Typical examples of hydrophobic group $R_1$ include alkyl chains comprising 1 to 30 carbon atoms, and alkoxylated groups notably comprising 1 to 10 units of ethylene oxide (—CH$_2$CH$_2$O—) groups A hydrophobic alcohol (I) according to the present invention is preferably an alcohol with a value P>1 according to the expression as defined below:

$P$=[alcohol $(I)$]$_{octanol}$/[alcohol $(I)$]$_{unionized\ water}$

A stock solution of the compound is prepared in either water pre-saturated with n-octanol or n-octanol pre-saturated with water. The concentration of this stock solution is known precisely before it is employed in the determination of the partition coefficient. In a separation flask, to a given volume of this solution is added the exact same volume of the other solvent (respectively n-octanol pre-saturated with water or water pre-saturated with n-octanol). After addition, the flask is hand shaken for 30 seconds. After separation of the two phases, the compound concentration is determined in each phase. This may be done by taking an aliquot of each of the two phases and analyzing them by the chosen procedure. The total quantity of substance present in both phases should be calculated and compared with the quantity of the substance originally introduced. The partition coefficient P is then calculated following the above equation.

Specific examples of the alcohol (I) include 2-ethylhexyl alcohol, octyl alcohol, decyl alcohol, lauryl alcohol (dodecanol), myristyl alcohol, palmityl alcohol, stearyl alcohol, isostearyl alcohol, oleyl alcohol, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monomethyl ether, polyethylene glycol monoethyl ether, polyethylene glycol monopropyl ether, polyethylene glycol monobutyl ether, polypropylene glycol monomethyl ether, polypropylene glycol monoethyl ether, polypropylene glycol monopropyl ether and polypropylene glycol monobutyl ether.

For the process of the present invention, the aforementioned examples of alcohols (I) may be used alone or in a mixture of any optional two or more thereof. For instance, the at least one alcohol (I) in the present invention may include lauryl alcohol, 2-ethylhexyl alcohol or isostearyl alcohol, and preferably includes lauryl alcohol.

As previously defined, the polyol (II) for the present invention is represented by the general formula (2):

$$R_2\text{—}(OH)_m \quad (2)$$

wherein $R_2$ represents the skeleton moiety of the polyol and m is an integer of from 2 to 20.

The radical $R_2$ may represent an alkyl, aryl, alkenyl or alkoxy radical comprising 1 to 36 carbon atoms, and optionally comprising one or several heteroatom(s) such as O or N. In one preferred embodiment, $R_2$ represents the skeleton moiety of a glycerol, with m being 3.

The polyol (II) may notably be a hydrophilic compound. A hydrophilic polyol (II) according to the present invention is preferably a compound with a value P<1 according to the expression as previously defined.

Specific examples of the polyol (II) preferably have 2 to 6 hydroxyl groups, and are selected from a group consisting of ethylene glycol, diethylene glycol, polyethylene glycol, propylene glycol, dipropylene glycol, polypropylene glycol, 1,4-butylene glycol, 1,6-hexylene glycol, 1,8-octylene glycol, 1,10-decylene glycol, neopentyl glycol, trimethylol ethane, trimethylol propane, glycerol, diglycerol, triglyceryl, pentaerythritol and sorbitol.

In one embodiment of the invention, the polyol (II) is a polyglycerol, defined as an oligomeric and/or polymeric chain composed of monomeric glycerol (i.e., $HOCH_2CH(OH)CH_2OH$) bonded together by ether linkages at the hydroxyl residue. From the view point of a good applicability of the resultant ether mixture, preferred polyol (II) is selected from glycerol, polyglycerol, and mixtures thereof. The preferred polyglycerols useful in the present invention have 2 to 20, preferably 2 to 10, and more preferably 3-6 glycerol units.

Generally, in the process invention as above defined, the molar ratio of polyol (II) to alcohol (I) is from 0.01 to 50, preferably from 0.5 to 10. More specifically, the molar ratio of hydrophilic polyol (II) to hydrophobic alcohol (I) is from 0.01 to 50, preferably from 0.5 to 10.

Moreover, the process invention as above defined also uses a polymer (F) as a catalyst (X), the polymer (F) is a polymer comprising recurring units derived from at least one ethylenically unsaturated monomer [monomer (M)] and bearing at least one cation exchange group.

The monomer (M) can notably be either hydrogenated (i.e. free of fluorine atom) [monomer (HM), hereinafter], or fluorinated (i.e. containing at least one fluorine atom) [monomer (FM), hereinafter], and can further comprise one or more other halogen atoms (Cl, Br, I).

Non limitative examples of monomer (FM) are notably tetrafluoroethylene (TFE), vinylidene fluoride (VdF), chlorotrifluoroethylene (CTFE), and mixtures thereof.

Non limitative examples of monomer (HM) are notably ethylene, propylene, vinyl monomers such as vinyl acetate, acrylic monomers, like methyl methacrylate, acrylic acid, methacrylic acid and hydroxyethyl acrylate, as well as styrene monomers, like styrene and p-methylstyrene.

Optionally, the polymer (F) may comprise recurring units derived from one first monomer, said first monomer being a monomer (M) as above described, and at least one other monomer [comonomer (CM), hereinafter]. Hereinafter, the term comonomer (CM) should be intended to encompass both one comonomer and two or more comonomers.

The comonomer (CM) can notably be either hydrogenated (i.e. free of fluorine atom) [comonomer (HCM), hereinafter] or fluorinated (i.e. containing at least one fluorine atom) [comonomer (FCM), hereinafter].

Non limitative examples of suitable hydrogenated comonomers (HCM) are notably ethylene, propylene, vinyl monomers such as vinyl acetate, acrylic monomers, like methyl methacrylate, acrylic acid, methacrylic acid and hydroxyethyl acrylate, as well as styrene monomers, like styrene and p-methylstyrene.

Non limitative examples of suitable fluorinated comonomers (FCM) are notably:

$C_3$-$C_8$ fluoro- and/or perfluoroolefins, such as hexafluoropropene, pentafluoropropylene, and hexafluoroisobutylene;

$C_2$-$C_8$ hydrogenated monofluoroolefins, such as vinyl fluoride;

1,2-difluoroethylene, vinylidene fluoride and trifluoroethylene;

perfluoroalkylethylenes complying with formula $CH_2=CH-R_{f0}$, in which $R_{f0}$ is a $C_1$-$C_6$ perfluoroalkyl;

chloro- and/or bromo- and/or iodo-$C_2$-$C_6$ fluoroolefins, like chlorotrifluoroethylene;

fluoroalkylvinylethers complying with formula $CF_2=CFOR_{f1}$ in which $R_{f1}$ is a $C_1$-$C_6$ fluoro- or perfluoroalkyl, e.g. —$CF_3$, —$C_2F_5$, —$C_3F_7$;

fluoro-oxyalkylvinylethers complying with formula $CF_2=CFOX_0$, in which $X_0$ is a $C_1$-$C_{12}$ oxyalkyl, or a $C_1$-$C_{12}$ (per)fluorooxyalkyl having one or more ether groups, like perfluoro-2-propoxy-propyl;

fluoroalkyl-methoxy-vinylethers complying with formula $CF_2=CFOCF_2OR_{f2}$ in which $R_{f2}$ is a $C_1$-$C_6$ fluoro- or perfluoroalkyl, e.g. —$CF_3$, —$C_2F_5$, —$C_3F_7$ or a $C_1$-$C_6$ (per)fluorooxyalkyl having one or more ether groups, like —$C_2F_5$—O—$CF_3$;

fluorodioxoles, of formula:

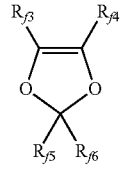

wherein each of $R_{f3}$, $R_{f4}$, $R_{f5}$, $R_{f6}$, equal or different each other, is independently a fluorine atom, a $C_1$-$C_6$ fluoro- or per(halo)fluoroalkyl, optionally comprising one or more oxygen atom, e.g. —$CF_3$, —$C_2F_5$, —$C_3F_7$, —$OCF_3$, —$OCF_2CF_{20}CF_3$.

Generally, the polymer (F) comprises a substantial amount of cation exchange groups which are effective to modify the chemical properties of the polymer (F).

As used herein, the term "cation exchange group" has its general meaning as intended in organic chemistry and it encompasses atoms or combination of atoms bonded to the carbon skeleton of the ethylenically unsaturated monomer of the polymer (F), which confers to said ethylenically unsaturated monomer ability to trap and release (i.e. exchange) cations in a process called ion exchange. Generally cation exchange groups are negatively charged moieties.

The choice of the cation bound to the negatively charged moiety is not critical. For example, cation exchange groups usually come with sodium ($Na^+$) or hydrogen ($H^+$) ions attached to said exchange sites. Both of these ions have generally low affinities to the sites. It is widely understood that when such exchange sites are exposed to appropriate conditions (e.g. in a reactive environment), cations can be replaced by protons so as to obtain an acid catalysts possessing labile $H^+$.

The polymer (F) has preferably linked on its cation exchange groups, hydrogen ($H^+$) ions.

Non limitative examples of cation exchange groups are notably those complying with formula:

$SO_2X$, wherein X is chosen among halogens (Cl, F, Br, I), —$O^-M^+$, wherein $M^+$ is a cation selected among $H^+$, $NH_4^+$, $K^+$, $Li^+$, $Na^+$, or mixtures thereof.

COY, wherein Y is chosen among halogens (Cl, F, Br, I); —$O^-M^+$, wherein $M^+$ is a cation selected among $H^+$, $NH_4^+$, $K^+$, $Li^+$, $Na^+$; —$OR_{Hy}$ wherein $R_{Hy}$ is a $C_1$-$C_6$ hydrocarbon group; —$OR_{Hf}$ wherein $R_{Hf}$ is a $C_1$-$C_6$ fluorocarbon or per(halo)fluorocarbon group; —$N(R_{Hy*})_2$, wherein $R_{Hy*}$, equal or different at each occurrence, is hydrogen or a $C_1$-$C_6$ hydrocarbon group, or mixtures thereof.

$PO_2Z$, wherein Z is chosen among halogens (Cl, F, Br, I); —$O^-M^+$, wherein $M^+$ is a cation selected among $H^+$, $NH_4^+$, $K^+$, $Li^+$, $Na^+$; —$OR_{Hy}$ wherein $R_{Hy}$ is a $C_1$-$C_6$ hydrocarbon group, and —$OR_{Hf}$, wherein $R_{Hf}$ is a $C_1$-$C_6$ fluorocarbon or per(halo)fluorocarbon group, or mixture thereof.

Preferably, in the abovementioned examples of cation exchange groups, each of X, Y and Z is independently —$O^-H^+$.

For the purpose of the invention, a preferred cation exchange group in polymer (F) complies with formula —$SO_2X$ as described above.

Polymer (F) comprises advantageously at least 1%, preferably at least 2%, more preferably at least 3%, even more preferably at least 5%, by mole of recurring units derived from at least one monomer bearing a cation exchange group ["functional monomer", hereinafter], based on the total moles of recurring units.

Polymer (F) comprises advantageously at most 75%, preferably at most 50%, more preferably at most 30%, even more preferably at most 25% by moles of recurring units derived from at least one functional monomer, based on the total moles of recurring units.

Preferably, the polymer (F) comprises recurring units derived from at least one functional monomer chosen among:

(M1) sulfonatedperfluoroolefin of formula (M1):

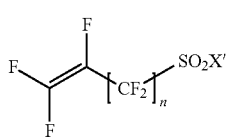

(M1)

wherein n is an integer between 0 and 6 and X' is chosen among halogens (Cl, F, Br, I), —$O^-M^+$, wherein $M^+$ is a cation selected among $H^+$, $NH_4^+$, $K^+$, $Li^+$, $Na^+$, or mixtures thereof; preferred sulfonatedperfluoroolefin are those complying with formulae (M1-A) and (M1-B):

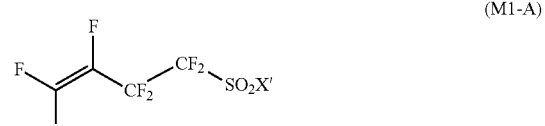

(M1-A)

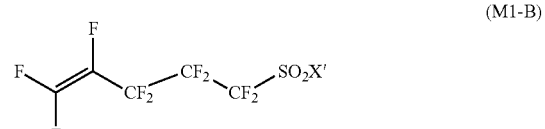

(M1-B)

wherein X' has the same meaning as above defined;

(M2) sulfonatedperfluorovinylethers of formula (M2):

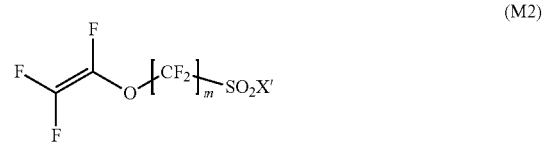

(M2)

wherein m is an integer between 1 and 10 and X' is chosen among halogens (Cl, F, Br, I), —$O^-M^+$, wherein $M^+$ is a cation selected among $H^+$, $NH_4^+$, $K^+$, $Li^+$, $Na^+$, or mixtures thereof; preferred are sulfonatedperfluorovinylethers of formulae (M2-A), (M2-B) and (M2-C):

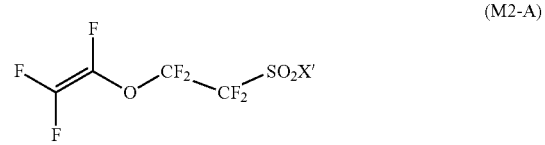

(M2-A)

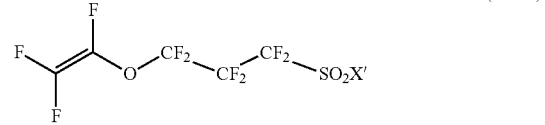

(M2-B)

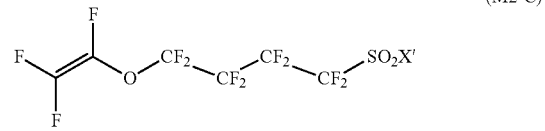

(M2-C)

wherein X' has the same meaning as above defined; most preferably, the sulfonatedperfluorovinylether is perfuoro-5-sulphonylfluoride-3-oxa-1-pentene (also known as "SFVE") of formula (M2-D):

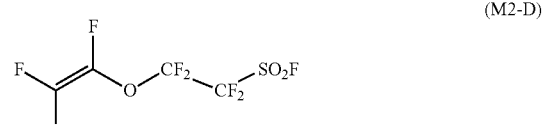

(M2-D)

which can be in its —$SO_2F$ form or in any of the —$SO_2X'$ forms, as above detailed;

(M3) sulfonatedperfluoroalkoxyvinylethers of formula (M3):

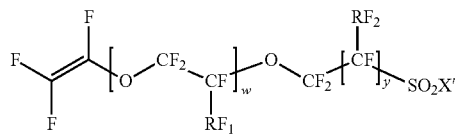

(M3)

wherein w is an integer between 0 and 2, $RF_1$ and $RF_2$, equal or different from each other and at each occurrence, are independently —F, —Cl or a $C_{1-10}$perfluoroalkyl group, optionally substituted with one or more ether oxygens, y is an integer between 0 and 6 and X' is chosen among H, halogens (Cl, F, Br, I), —O$^-$M$^+$, wherein M$^+$ is a cation selected among H$^+$, NH$_4^+$, K$^+$, Li$^+$, Na$^+$, or mixtures thereof; preferably X' is fluorine; preferred sulfonatedperfluoroalkoxyvinylether complies with formula (M3) here above, wherein w is 1, $RF_1$ is —$CF_3$, y is 1 and $RF_2$ is —F and X' is F [formula (M3-A), also called "PSEPVE" (perfluoro-2-(2-fluorosulfonylethoxy)propylvinyl ether)]:

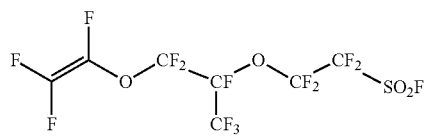

(M3-A)

which can be in its —SO$_2$F form or in any of the —SO$_2$X' forms, as above detailed;

(M4) perfluoroalkoxyvinylether carboxylates of formula (M4):

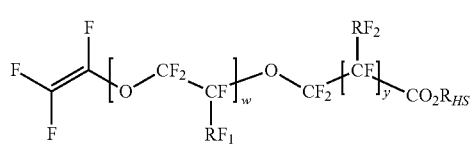

(M4)

wherein w, y, $RF_1$ and $RF_2$ have the same meaning as above defined, and $R_{HS}$ is a $C_{1-10}$ alkyl or fluoroalkyl group; preferred perfluoroalkoxyvinylether carboxylate complies with formula (M4) here above, wherein w is 0, y is 2, $R_{HS}$ is methyl and $RF_2$ is —F [formula (M4-A)]:

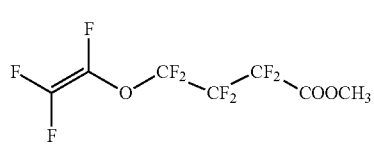

(M4-A)

(M5) sulfonated aromatic (per)fluoroolefins of formula (M5):

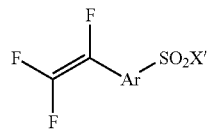

(M5)

wherein Ar is a $C_{3-15}$ aromatic or heteroaromatic moiety and X' is chosen among halogens (Cl, F, Br, I), —O$^-$M$^+$, wherein M$^+$ is a cation selected among H$^+$, NH$_4^+$, K$^+$, Li$^+$, Na$^+$, or mixtures thereof; and (M6) mixtures thereof.

Optionally, the polymer (F) can further comprise recurring units derived from bis-olefins of formula:

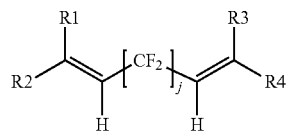

wherein j is an integer between 2 and 10, preferably between 4 and 8, and R1, R2, R3, R4, equal or different from each other, are H or $C_{1-5}$ alkyl or fluoroalkyl groups.

Should the polymer (F) comprise recurring units derived from a bis-olefin as above defined, it advantageously comprises said recurring units in an amount in the range from 0.01 to 5% by mole, with respect to all recurring units of polymer (F).

In one preferred embodiment, the polymer (F) is a functional per(halo)fluoropolymer. For the purpose of the invention, the term "functional per(halo)fluoropolymer" is intended to denote a functional fluoropolymer substantially free of hydrogen atoms.

The term "substantially free of hydrogen atom" is understood to mean that the functional per(halo)fluoropolymer consists essentially of:

recurring units derived from one or more than one ethylenically unsaturated monomer comprising at least one fluorine atom and free from hydrogen atoms (per(halo)fluoromonomer, hereinafter); and recurring units derived from one or more than one ethylenically unsaturated monomer comprising at least one fluorine atom and at least one cation exchange group, and free from hydrogen atoms (except those optionally comprised in the cation exchange group) (functional per(halo)fluoromonomer, hereinafter).

The per(halo)fluoromonomer and the functional per(halo)fluoromonomer may be the same or different monomers, that is to say that the functional per(halo)fluoropolymer can be a homopolymer of a functional per(halo)fluoromonomer, or can be a copolymer of one or more than one per(halo)fluoromonomer and one or more than one functional per(halo)fluoromonomer.

Preferred polymer (F) is chosen among functional per(halo)fluoropolymers comprising (preferably consisting essentially of) recurring units derived from at least one functional per(halo)fluoromonomer and at least one per(halo)fluoromonomer chosen among:

$C_3$-$C_8$perfluoroolefins, preferably tetrafluoroethylene (TFE) and/or hexafluoropropylene (HFP);

chloro- and/or bromo- and/or iodo-$C_2$-$C_6$ per(halo)fluoroolefins, like chlorotrifluoroethylene (CTFE) and/or bromotrifluoroethylene;

perfluoroalkylvinylethers (PAVE) complying with formula $CF_2=CFOR_{f1}$ in which $R_{f1}$ is a $C_1$-$C_6$perfluoroalkyl, e.g. —$CF_3$, —$C_2F_5$, —$C_3F_7$; and perfluoro-oxyalkylvinylethers complying with formula $CF_2=CFOX_0$, in which $X_0$ is a $C_1$-$C_{12}$perfluorooxyalkyl having one or more ether groups, like perfluoro-2-propoxy-propyl More preferred polymer (F) is chosen among tetrafluoroethylene (TFE) copolymers comprising (preferably consisting essentially of) recurring units derived from at least one functional per(halo)fluoromonomer as above defined.

Preferred functional per(halo)fluoromonomer are notably sulfonatedperfluorovinylethers of formula (M2) as above detailed and sulfonatedperfluoroalkoxyvinylethers of formula (M3) as above detailed, and mixtures thereof.

Even more preferred polymer (F) is selected among TFE copolymers comprising (preferably consisting essentially at) recurring units derived from PSEPVE (formula M3-A here above) and/or SFVE (formula M2-D here above), in their —$SO_2F$ or —$SO_2X''$ form, wherein X" is chosen among halogens (Cl, Br, I), —$O^-M^+$, wherein $M^+$ is a cation selected among $H^+$, $NH_4^+$, $K^+$, $Li^+$, $Na^+$, or mixtures thereof; preferably in their —$SO_3H$ form.

Still more preferred polymer (F) is selected among TFE copolymers comprising (preferably consisting essentially at):

from 5 to 25% by moles of recurring units derived from PSEPVE and/or SFVE, in their —$SO_2F$ or —$SO_2X''$ form, wherein X" is chosen among halogens (Cl, Br, I), —$O^-M^+$, wherein $M^+$ is a cation selected among $H^+$, $NH_4^+$, $K^+$, $Li^+$, $Na^+$, or mixtures thereof; preferably in their —$SO_3H$; and from 95 to 75% by moles of recurring units derived from TFE.

According to a preferred embodiment of the invention, the polymer (F) is chosen among TFE copolymers as above described wherein the functional monomer is SFVE, in its —$SO_2F$ or —$SO_2X''$ form, wherein X" is chosen among halogens (Cl, Br, I), —$O^-M^+$, wherein M is a cation selected among $H^+$, $NH_4^+$, $K^+$, $Li^+$, $Na^+$, or mixtures thereof; preferably in its —$SO_3H$ form.

Furthermore, the polymer (F) may be used in the form of an ion-exchange resin. For the purpose of the present invention, the term "ion-exchange resin" is intended to denote a solid insoluble matrix (or support structure), normally in the form of beads of reduced size (e.g. from 0.5 to 5 mm), generally fabricated from an organic polymer substrate, on the surface of which are active sites (ion-exchange sites) which easily trap and release ions in the ion exchange process.

When used as the polymer matrix of an ion-exchange resin, the polymer (F) preferably comprises recurring units derived from styrene (so-called polystyrene matrix) or recurring units derived from a (meth)acrylic ester (so-called acrylic matrix). The required exchange sites can be introduced after polymerization, or substituted monomers can be used. Preferably the polymer matrix is a crosslinked matrix, and the crosslinking is usually achieved by adding a small proportion of divinylbenzene during polymerization. More preferably the polymer matrix is a crosslinked polystyrene matrix.

In one preferred embodiment for the present invention, the polymer (F) is used in the form of a cation exchange resin, which has cation-exchange groups on its surface. Useful cation-exchange resins include polymers (typically cross-linked) that have a plurality of pendant anionic or acidic groups such as, for example, polysulfonates or polysulfonic acids, polycarboxylates or polycarboxylic acids. Preferred polymers (F) used in the form of cation exchange resins include, for example, sulfonated styrene-divinylbenzene copolymers, sulfonated crosslinked styrene polymers, phenol-formaldehyde-sulfonic acid copolymers, and benzene-formaldehyde-sulfonic acid copolymers.

Cation-exchange resins are available commercially. Examples of suitable commercially available cation-exchange resins include: resins having the trade designations "AMBERJET 1200", "AMBERLITE IR-120", "AMBERLITE IR-122", or "AMBERLITE 132 E" available from Rohm and Haas Company, Philadelphia. Pa.; resins having the trade designations "DIAION SK 1B" and "DIAION SK 110" available from Mitsubishi Chemical, Tokyo, Japan; resins having the trade designations "DOWEX HCR-W2", "DOWEX HCR-S", and "DOWEX 650C", available from Dow Chemical Company, Midland, Mich.; resins having the trade designations "IONAC C-249", "IONAC C-253", "IONAC C-266", and "IONAC C-267"; and resins having the trade designations "LEWATIT S 100", "LEWATIT S 100H" (acid form), "LEWATIT S 110", "LEWATIT S110H" (acid form), "LEWATIT S 1468", "LEWATIT MONOPLUS SP 112", "LEWATIT MONOPLUS SP 112" (acid form), "LEWATIT S 2568", and "LEWATIT S 2568H" (acid form), all available from Sybron Chemicals, Inc.; and resins having the trade designations "PUROLITE C-100", "PUROLITE C-100 E", "PUROLITE C-100×10", and "PUROLITE C-120 E" available from The Purolite Company; and styrene resins having the trade designations "732 Cation exchange resin" available from many mainland China suppliers. It is expected that other products of the same type would be equally satisfactory.

Cation-exchange resins such as those described above are commonly supplied commercially in the acid or sodium form. If the cation-exchange resin is not in the acid form (i.e. protonated form) it should be at least partially converted, typically fully converted, to the acid form in order to avoid the generally undesired introduction of other cations into the dispersion. This conversion to the acid form may be accomplished by means well known in the art, for example by treatment with any adequately strong acid.

It has been surprisingly found out that the polymer (F) according to the aforementioned preferred embodiments possess a good thermal stability and improved catalytic behaviour in the etherification process of the present invention, and is conveniently used in the solid state, thus being easily separated, recovered and recycled.

Moreover, the polymer (F) also advantageously provides a large group of effective acidic catalysts for the etherification process of the present invention, with a wide range of acidity for selection in different industrial applications.

For the purpose of the present invention, the polymer (F) can be used either as unsupported or supported catalysts (X), under different forms including, for example, flakes, powder, pellets, beads, and membranes. When catalysts (X) are used as membranes, it is also possible to take benefit of additional advantages, e.g. linked to the separation of the reactants and/or of the products at the opposite side of the membrane, with consequent displacement of reaction equilibria and increase of kinetics. Should the catalyst (X) be used in the form of pellets, it is generally immobilized in the reactor as fixed bed or it can be dispersed in the reactive medium. In said latter circumstance it can be easily separated from the reaction mixture, e.g. by filtration.

Noticeably, the polymer (F) may be grafted or supported to solid particles having a medium diameter between 2 and 200 nm, preferably between 10 and 50 nm. The shape of said solid particles can be generally spherical, cubic, platy, or acicular (elongated or fibrous). The particle diameter can be determined by visually examining a micrograph of a transmission electron microscopy (TEM) image of the particles, measuring the particle diameters therein, and calculating the average primary particle size of the measured particles based on magnification of the TEM image.

Suitable solid particles serving for this purpose may be made of inorganic material such as water insoluble metal salt, metal hydroxide, metal oxide, mixed metal oxide, clay, or phosphate or a hydrogenophosphate of metals or rear earths. Unlimited examples of said suitable solid particles include bentonite, tin oxide, magnesium aluminium silicate, magnesium oxide, titanium oxide, barium sulphate and silica, such as those described in U.S. Pat. No. 4,833,060 (EASTERMAN KODAK COMPANY) Mar. 21, 1988 at column 4, lines 54-61, and alumina as described in US 20050156340 A (E INK CORPORATION) Jan. 19, 2005. Alternatively, said solid particles may be made of organic material and obtained from reticulation of polymer chains such as latex particles, polymeric nanoparticles with core-shell structures which are composed by amphiphilic chains at the core or on the layer of the shell.

In a preferred embodiment, the polymer (F) has at least one organic chain linked to the surface of said solid particles via covalent bond, typically via oxygen atoms initially present in a hydroxyl metal group on the solid particle surface. In this case, the particles may be formed at least partially of silicon oxide, oxy-hydroxide of aluminium and/or titanium oxide.

Specifically, as demonstrated in the working Examples of the following text, the Applicant found that the polymer (F) which comprises recurring units derived from styrene can be conveniently used as a supported Catalyst (X), and be grafted or supported to solid particles having a medium diameter between 2 and 200 nm, preferably between 10 and 50 nm, as aforementioned.

In specific embodiments of the present invention, the amount of catalyst (X) used is from 0.1 to 30%, preferably from 1 to 15%, and more preferably from 3 to 10%, equivalent of the alcohol (I) reactant.

In the process of the present invention, the etherification reaction temperature may be comprised between 50 and 250° C., preferably between 100 and 200° C., more preferably between 130 and 170° C.

Advantageously, in the process of the present invention, the etherification reaction may be performed in the absence of a solvent. Optionally, according to practical need, a solvent can also be present in the etherification reaction, preferably a polar solvent such as water, urea, an imide solvent (e.g. pyridine), and a solvent of amide series (e.g. N-methyl-2-pyrrolidone, or NMP).

Preferably, the medium used in the process of the present invention is substantially free or, in some cases, completely free of any surfactant, at the start of the reaction. As used herein, the term "surfactant" refers to materials that have an amphiphilic molecular structure, which includes a polar hydrophilic molecular moiety and a nonpolar lipophilic molecular moiety, and which acts to lower the interfacial tension between the dispersed phase and the continuous phase in an emulsion. As will be appreciated, surfactants can be classified as ionic (anionic, cationic, and amphoteric) or nonionic. As used herein, the term "substantially free" when used with reference to the absence of surfactant in the medium of the present invention, means that the emulsion comprises less than 0.1% wt of surfactant, based on the total weight of the medium, notably at the beginning of the reaction; and preferably during the reaction. As used herein, the term "completely free" when used with reference to the absence of surfactant in the medium of the present invention, means that the emulsion comprises no surfactant at all.

A specific embodiment of the process invention comprises the steps below:
a) mixing the at least one alcohol (I), the at least one polyol (II), and the catalyst (X);
b) proceeding to the reaction of the ether compound by setting a temperature (T); and
c) isolating the ether compound.

In step a), the alcohol (I) and polyol (II) reactants and the catalyst (X) are typically combined in a reaction vessel and stirred to constitute a reaction mixture.

In step b), the etherification reaction is led by setting an appropriate temperature (T). The selection of the appropriate temperature (T) is linked to the nature of alcohol (I) and polyol (II), and is generally comprised between 50 and 250° C., preferably between 100 and 200° C., more preferably between 130 and 170° C.

In step b), several stirring methods may be used during the reaction; preferably a continuous stirring is maintained in this step. During the step b), the reaction may be carried out under an atmospheric pressure or, preferably, under a vacuum pressure of 100 mbar to 600 mbar. Said reaction can be made under inert gas or air.

Exemplary reaction time for step b) is between 1 to 72 hours, preferably 12 to 48 hours.

In step c), isolation of the ether compound can be realized by any separation methods known in the art, such as but unlimited to extraction, distillation, and/or crystallization.

Notably when reaction of the present invention permits to obtain a MAGE as the ether compound, the isolation step c) may be carried out according to the following steps:
c1) adding an ethanol, water or mixture thereof into the reaction mixture obtained from step b);
c2) neutralizing the resultant solution of step c1) and filtering to obtain a filtrate;
c3) washing the filtrate obtained from step c2) with a polar solvent;
c4) concentrating the washed filtrate obtained from step c3) to obtain a concentrated liquid; and,
c5) drying the concentrated liquid from step c4) and obtain a crude MAGE compound.

Preferably, in the step c5) as above described, the drying is performed under a vacuum pressure.

In a second aspect, the present invention also relates to a product susceptible to be obtained by the etherification process as afore-described.

GC, HPLC/MS analysis of the final product obtained from the afore-described etherification process reveals that the thus resulted mixture is a composition characterized by including:
(i) more than one ether compound of formula (3) [ether (E1)],

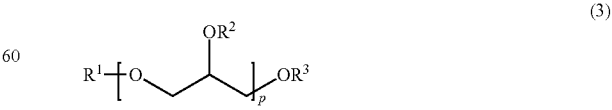

(3)

wherein: p is an integer from 1 to 36, and radicals $R^1$, $R^2$, and $R^3$, being same or different, are independently a hydrogen atom or a hydrocarbon group having 1 to 36 carbon atoms and optionally containing oxygen atom, provided that $R^2$ and $R^3$ are not hydrogen at the same time, and wherein $R^2$ optionally join together with $R^1$ or $R^3$ to form at least one oxygen-containing cyclic group having 3 to 7 carbon atoms;
(ii) at least one polyol (II) compound represented by the general formula (2):

  (2)

wherein $R_2$ represents the skeleton moiety of the polyol and m is an integer of from 2 to 20; and,
(ii) optionally, at least one mono alkyl glyceryl ether (MAGE) compound of formula (4):

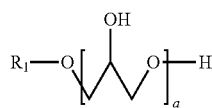  (4)

wherein a is an integer of from 1 to 20, and radical $R_1$ is a hydrocarbon group having 1 to 36 carbon atoms, as defined above.

Preferably, in the aforedescribed composition, the ether (M1) components contain at least one ether compound of formula (5) [ether (E1-A)]:

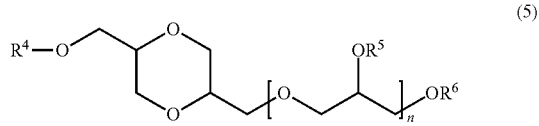  (5)

wherein: n is an integer from 0 to 36, and radicals $R^4$, $R^5$ and $R^6$, being same or different, are independently a hydrogen atom or a hydrocarbon group having 1 to 36 carbon atoms and optionally containing oxygen atom, wherein $R^5$ optionally join together with $R^4$ or $R^6$ to form at least one oxygen-containing cyclic group having 3 to 7 carbon atoms.

It has been surprisingly found out that, without further purification such as removing the excess, unreacted polyol (II) compound or separating the MAGE compounds from ether components (E1), the composition product obtained by the afore-described etherification process has an excellent surfactant property and can be conveniently used for a great many industrial applications.

Thus, in yet another aspect of the present invention, it is directed to a surfactant composition [composition (S)] comprising:
(i) more than one ether compound of formula (3) [ether (E1)],

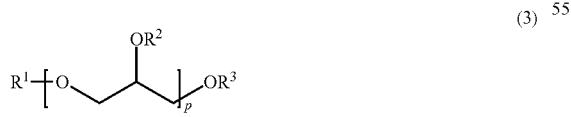  (3)

wherein: p is an integer from 1 to 36, and radicals $R^1$, $R^2$, and $R^3$, being same or different, are independently a hydrogen atom or a hydrocarbon group having 1 to 36 carbon atoms and optionally containing oxygen atom, provided that $R^2$ and $R^3$ are not hydrogen at the same time, and wherein $R^2$ optionally join together with $R^1$ or $R^3$ to form at least one oxygen-containing cyclic group having 3 to 7 carbon atoms;
(ii) at least one polyol (II) compound represented by the general formula (2):

  (2)

wherein $R_2$ represents the skeleton moiety of the polyol and m is an integer of from 2 to 20; and,
(ii) optionally, at least one mono alkyl glyceryl ether (MAGE) compound of formula (4):

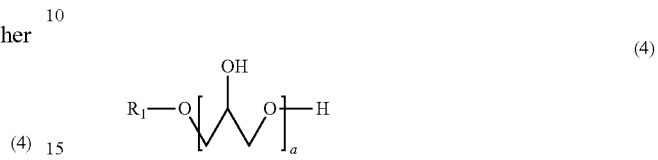  (4)

wherein a is an integer of from 1 to 20, and radical $R_1$ is a hydrocarbon group having 1 to 36 carbon atoms, as defined above.

Preferably, in the composition (S), the ether (M1) components contain at least one ether (E1-A) compound of formula (5) as above defined.

Additionally, composition (S) may further comprise at least one commercially available anionic surfactant ingredient, or other additives such as betaines and quats to tailor the surfactant performance of composition (S).

In still another aspect of the invention, it is directed to the use of said composition (S) in the applications for home care or personal care, or other industrial applications requiring surfactant activity. Unlimited examples of said applications include laundry detergents, fabric conditions, cosmetic ingredients, toiletries including shampoos, liquid soaps, creams, lotions, balms, ointments, antiseptics, dentifrices and styptics, and other personal care formulations or agriculture additives.

DESCRIPTION OF EMBODIMENTS

The present invention will be further illustrated with reference to the following examples.

EXAMPLES

Raw Materials

NAFION® NR50 polymer: a TFE/PSEPVE copolymer commercially available from Aldrich.
Aquivion® D66-20BSX polymer: a TFE/SFVE copolymer in pellet form, available from Solvay Specialty Polymers Italy S.p.A.
732 Cation exchange resin: a sulfonated styrene-divinylbenzene copolymer from Sinopharm Chemical Reagent Co., Ltd
AEO7: Fatty alcohol polyoxyethylene (7) ether from Rhodia, Rhodasurf L-7/90.
MAGE4: Dodecyl polyglyceryl ether from Daicel Chemical Industries Ltd.

Preparation and Characterization of Ether Compositions

Example 1

Etherification of Glycerol and Dodecanol with a TFE/PSEPVE Copolymer as Catalyst In a 20 mL Schlenk tube fitted with inside water trap, dodecanol (1.60 g), glycerol (3.16 g) and Nafion® NR50 (0.58 g, 6% eq. to dodecanol) were added. The reaction mixture was vigorously stirred at 150° C. for 24 hrs under static vacuum. After the mixture cooled, pyridine was added to neutralize the catalyst, then precipitated in large excess of THF/diethyl ether (1:1). The obtained solution was concentrated by a rotavap. After most of dodecanol were removed through distillation under high vacuum, the residue was dissolved in methanol/H$_2$O (10:1 V:V) solution, further washed with heptane. The remaining solution was concentrated by rotavap and further dried in vacuum oven at 50° C. overnight. 1.92 g of viscous product was obtained.

GC analysis wt %: C12OH=0.75; MAGE1=0.31; DE=0.15; MAGE2=2.28.

$^1$H NMR (CDCl$_3$): 0.9 ppm (t, 3H, —CH$_3$ of dodecane groups), 1.3 ppm (s, 17.99H, CH$_3$—CH$_2$—CH$_2$— of dodecane groups), 1.65 ppm (sextuplet, 2.77H, CH$_3$—CH$_2$—CH$_2$— of dodecane groups), 3.25-4.20 ppm (m, 14.77H, —CH$_2$—O and >CHO— glyceryl units and dodecyl group).

Example 2

Etherification of Glycerol and Dodecanol with a TFE/SFVE Copolymer as Catalyst

In a 250 mL two-neck round-bottomed flask fitted with magnetic stir bar and a water trap on one neck, dodecanol (24.1 g), glycerol (47.8 g) and Aquivion® D66-20BSX (4.44 g, 6% eq. to dodecanol) were added. The reaction mixture was vigorously stirred at 150° C. for 24 hrs under static vacuum. After the mixture cooled, pyridine was added to neutralize the catalyst, then precipitated in large excess of THF/diethyl ether (1:1). The obtained solution was concentrated by rotavap. After most of dodecanol was removed through distillation under high vacuum, the residue was dissolved in methanol/H$_2$O (10:1 V:V), further washed with heptane. The remaining solution was concentrated by rotavap and further dried in vacuum oven at 50° C. overnight. 23.0 g of viscous product was obtained. The obtained product was characterized by $^1$H NMR, GC and HPLC to get the average compositions which was listed in Table 1.

Example 3

Etherification of Glycerol and Dodecanol with a TFE/SFVE Copolymer as Catalyst

In a 250 mL jacket reactor fitted with mechanic stir and a water trap on one neck, dodecanol (16.0 g), glycerol (32.6 g) and Aquivion® D66-20BSX (2.94 g, 6% eq. to dodecanol) were added. The reaction mixture was vigorously stirred at 150° C. for 18 hrs under moderate vacuum (200 mbar). After the mixture cooled, pyridine was added to neutralize the catalyst, then precipitated in large excess of THF/diethyl ether (1:1). The obtained solution was concentrated by rotavap. After most of dodecanol was removed through distillation under high vacuum, the residue was dissolved in methanol/H$_2$O (10:1 V:V), further washed with heptane. The remaining solution was concentrated by rotavap and further dried in vacuum oven at 50° C. overnight. 20.0 g of viscous product was obtained. The obtained product was characterized by $^1$H NMR, GC and HPLC to get the analysis results listed in Table 1.

Example 4

Etherification of Triglycerol and Dodecanol with a TFE/SFVE Copolymer as Catalyst In a 250 mL two-neck round-bottomed flask fitted with magnetic stir bar and a water trap on one neck, dodecanol (20.0 g), triglycerol (39.5 g) and Aquivion® D66-20BSX (2.11 g, 3% eq. to dodecanol) were added. The reaction mixture was vigorously stirred at 156° C. for 23 hrs under static vacuum. After the mixture cooled, diluted with THF and neutralized by pyridine, then centrifuged to remove insoluble polyglycerol and catalysts. The concentrated mixture from solution was diluted in 90 mL of MeOH and 30 mL of water, the product is extracted twice with 30 mL of heptane, then concentrated and dried overnight in the oven, 38.92 g of product was obtained as a highly viscous oil. The thus obtained product was characterized by $^1$H NMR, GC and HPLC to get the analysis results listed in Table 1.

Example 5

Etherification of Triglycerol and Dodecanol with a TFE/SFVE Copolymer as Catalyst In a 250 mL two-neck round-bottomed flask fitted with magnetic stir bar and a water trap on one neck, dodecanol (15.0 g), triglycerol (44.5 g) and Aquivion® D66-20BSX (1.59 g, 3% eq. to dodecanol) were added. The reaction mixture was vigorously stirred at 156° C. for 34.5 hrs under static vacuum. After the mixture cooled, diluted with THF and neutralized by pyridine, then centrifuged to remove insoluble polyglycerol and catalysts. The concentrated mixture from solution was diluted in 90 mL of MeOH and 30 mL of water, the product is extracted twice with 30 mL of heptane, then concentrated and dried overnight in the oven, 36.82 g of product are obtained as a very viscous oil. The obtained product was characterized by $^1$H NMR, GC and HPLC to get the analysis results listed in Table 1.

Example 6

Etherification of Triglycerol and Dodecanol with a TFE/SFVE Copolymer as Catalyst In a 250 mL two-neck round-bottomed flask fitted with magnetic stir bar and a water trap on one neck, dodecanol (11.0 g), triglycerol (43.5 g) and Aquivion® D66-20BSX (1.30 g, 3% eq. to dodecanol) were added. The reaction mixture was vigorously stirred at 156° C. for 20 hours under static vacuum. After the mixture cooled, diluted with THF and neutralized by pyridine, then centrifuged to remove insoluble polyglycerol and catalysts. The concentrated mixture from solution was diluted in 90 mL of MeOH and 30 mL of water, the product is extracted twice with 30 mL of heptane, then concentrated and dried overnight in the oven, 36.1 g of product are obtained as a very viscous oil. The obtained product was characterized by $^1$H NMR, GC and HPLC to get the analysis results listed in Table 1.

Example 7

Etherification of Glycerol and Dodecanol with a TFE/SFVE Copolymer as Catalyst

In a 250 mL two-neck round-bottomed flask fitted with magnetic stir bar and a water trap on one neck, glycerol (44.6 g) and Aquivion® D66-20BSX (1.34 g) were added. The mixture was dehydrated at 156° C. with stirring for 18.5 hours, about 7.14 g of water was collected. 15.01 g of dodecanol are added to the mixture and the system again was sealed under vacuum as before, continued being reacted for another 35 hours. After the mixture cooled, diluted with THF and neutralized by pyridine, then centrifuged to remove insoluble polyglycerol and catalysts. The concentrated mixture from solution was diluted in 90 mL of MeOH and 30 mL of water, the product is extracted twice with 30 mL of heptane, then concentrated and dried overnight in the oven, 33.1 g of product are obtained as a very viscous oil. The obtained product was characterized by $^1$H NMR, GC and HPLC to get the analysis results listed in Table 1.

Example 8

Etherification of Glycerol and Dodecanol with a TFE/SFVE Copolymer as Catalyst

In a 250 mL two-neck round-bottomed flask fitted with magnetic stir bar and a water trap on one neck, glycerol (47.5 g) and Aquivion® (1.42 g) were added. The mixture was dehydrated at 156° C. with stirring for 18 h30, about 6.24 g of water was collected. 12.01 g of dodecanol are added to the mixture and the system again was sealed under vacuum as before, continued being reacted for another 16 hours. After the mixture cooled, diluted with THF and neutralized by pyridine, then centrifuged to remove insoluble polyglycerol and catalysts. The concentrated mixture from solution was diluted in 90 mL of MeOH and 30 mL of water, the product is extracted twice with 30 mL of heptane, then concentrated and dried overnight in the oven, 35.5 g of product are obtained as a very viscous oil. The obtained product was characterized by $^1$H NMR, GC and HPLC to get the analysis results listed in Table 1.

Example 11

Etherification of Glycerol and Dodecanol with a Strong Acidic Polystyenic Exchange Resin as Catalyst In a 20 mL Schlenk tube fitted with inside water trap, dodecanol (1.60 g), glycerol (3.16 g) and 732 Cation exchange resin (0.19 g, 10% eq. to dodecanol) were added. The reaction mixture was vigorously stirred at 150° C. under static vacuum for 48 hrs. After the mixture was cooled and diluted with THF, the catalyst was collected by centrifuge. The obtained solution was concentrated by rotavap. After most of dodecanol were removed through distillation under high vacuum, the residue was dissolved in methanol/$H_2O$ (10:1 V:V), further washed with heptane. The remaining solution was concentrated by rotavap and further dried in vacuum oven at 50° C. overnight. 1.82 g of viscous product was obtained.

GC analysis wt %: C12OH=0.75; MAGE1=0.31; DE=0.15; MAGE2=2.28.

$^1$H NMR (CDCl$_3$): 0.9 ppm (t, 3H, —CH$_3$ of dodecane groups), 1.3 ppm (s, 17.99H, CH$_3$—CH$_2$—CH$_2$— of dodecane groups), 1.65 ppm (sextuplet, 2.77H, CH$_3$—CH$_2$—CH$_2$— of dodecane groups), 3.25-4.20 ppm (m, 14.77H, —CH$_2$—O and >CHO— glyceryl units and dodecyl group).

Example 12

Etherification of Glycerol and Dodecanol with a Strong Acidic Polystyrenic Exchange Resin as Catalyst In a 20 mL Schlenk tube fitted with inside water trap, glycerol (6.32 g) and 732 Cation exchange resin (0.19 g, 0.9 eq. H$^+$) were added. The reaction mixture was vigorously stirred at 150° C. under static vacuum for 12 hrs. Then, dodecanol (1.60 g) was added to the produced mixture, and the system again was sealed under vacuum as before, continued being reacted for another 16 hours. After the mixture cooled, diluted with mixture of water and methanol (20 mL, 10:1, v/v), the catalysts were recovered through centrifugation. The solution was extracted twice with 10 mL of heptane, then concentrated and dried overnight in the oven. 4.5 g of product was obtained as a very viscous oil.

GC analysis wt %: C$_{12}$OH=1.75; MAGE1=0.51; DE=0.35; MAGE2=3.28.

$^1$H NMR (CDCl$_3$): 0.9 ppm (t, 3H, —CH$_3$ of dodecane groups), 1.3 ppm (s, 17.99H, CH$_3$—CH$_2$—CH$_2$— of dodecane groups), 1.65 ppm (sextuplet, 2.77H, CH$_3$—CH$_2$—CH$_2$— of dodecane groups), 3.25-4.20 ppm (m, 18.6, —CH$_2$—O and >CHO— glyceryl units and dodecyl group).

TABLE 1

Composition characterized by $^1$H NMR, GC and HPLC (wt %)

| Sample | C12—OH (%)$^a$ | C12-ether (%)$^a$ | (P)glycerol (%)$^b$ | Ether product (%)$^c$ | Effective G/D molar ratio$^d$ |
|---|---|---|---|---|---|
| Ex. 2 | 0.71 | n.d.* | 12.9 | 86.4 | 1.43 |
| Ex. 3 | 1.69 | 0.48 | 11.2 | 86.6 | 3.24 |
| Ex. 4 | 4.01 | 1.74 | 13.6 | 80.0 | 3.43 |
| Ex. 5 | 2.06 | 0.67 | 34.2 | 62.3 | 3.79 |
| Ex. 6 | 0.55 | 0.24 | 41.4 | 57.9 | 3.90 |
| Ex. 7 | 1.55 | 0.60 | 14.2 | 83.1 | 3.75 |
| Ex. 8 | 1.52 | 0.16 | 22.0 | 76.3 | 4.64 |

*not detectable
$^a$The weight concentrations of dodecanol (C12—OH) and dodecyl ether (C12-ether) were analysed by GC
$^b$(P)glycerol concentration was analysed by HPLC
$^c$The weight concentration of the ether products formed by (poly)glycerol and dodecanol reactants in each Example was deducted from the measured weight concentrations of dodecanol (C12—OH), dodecyl ether (C12-ether), and (P)glycerol.
$^d$The ratio of glyceryl to dodecyl (G/D) in the product was obtained from $^1$H NMR characterization data after subtracting the contribution of impurities, i.e. C12—OH, C12-ether and (P)glycerol.

Properties of the obtained ether compositions are detailed in Table 2 below, in which several commercially available surfactants (AEO7 and MAGE4) were used for comparison of surfactant properties with the ether compositions obtained by Examples 2-8.

TABLE 2

| Sample | CMC (%)$^e$ | ST at CMC (mN/m)$^e$ | Foam at 2.5 g/l (mm)$^f$ |
|---|---|---|---|
| Ex. 2 | NA | 28 | 67 |
| Ex. 3 | NA | 25 | 23 |
| Ex. 4 | 0.068 | 28 | 85 |
| Ex. 5 | 0.053 | 27 | 105 |
| Ex. 6 | 0.093 | 28 | 117 |
| Ex. 7 | 0.050 | 29 | 57 |
| Ex. 8 | 0.142 | 27 | 85 |
| AEO7 | 0.023 | 32 | 143 |
| MAGE4 | 0.024 | 31 | 150 |

$^e$Critical Micelle Concentration (CMC) and Surface Tension (ST) at CMC was measured on a Sigma 700 tensiometer from BiolinScientific AB equipped with a Wilhelmy plate and a Du Noüy ring
$^f$Foam height was tested by the standard Ross-Miles method, using a 2.5 g/L test solution.

As seen from Table 2, the ether compositions obtained from Examples 2-8 according to the present invention achieved equally good surfactant properties as the two commercially available surfactants, especially in terms of surface tension and Ross mile foam height. Noticeably, Examples 4-7 each obtained a same level of critical micelle concentration (CMC) compared with benchmarks of AEO7 and MAGE4. Ross mile foam height of examples 5-6 is also similar to benchmarks. Significantly, the surface tension at CMC of example 2-8 is even lower than the benchmarks.

Additionally, wash tests on primary detergency of the ether composition products were carried out by measuring the amount of stain removed from regulated prestained soil cloths, in comparison with the abovementioned benchmarks of AEO7 and MAGE4. The different stains were recorded by the following codes:

JB01—carbon black with oil on cotton cloth
JB02—egg protein on cotton cloth
JB03—sebum on cotton cloth
CS61—Beef lard on cotton cloth
EMPA—lipstick on cotton cloth
20C—pigment, lanolin on polyester/cotton 65/35 cloth
20D—pigment, sebum on polyester/cotton 65/35 cloth
20PF—pigment, vegetable fat on polyester/cotton 65/35 cloth
30C—pigment, lanolin on polyester cloth
30D—pigment, sebum on polyester cloth
30PF—pigment, vegetable fat on polyester cloth The wash tests were performed with a Launderometer with the test conditions summarized below:
0.5 L of 250 ppm hard water
Washing temperature: 30° C.
Duration: 1 hour
Detergent concentration: 1 g/L
Performance measurement: L value (à lightness)
Prestained cloth samples: 5×5 cm, 4 pieces per type Table 3 showed the accumulative detergency performance on cotton, cotton & polyester and polyester cloth samples, for Examples 2-8 and the commercial samples of AEO7 and MAGE4. Specifically, the data in Table 3 indicated the average stain removal rate for different prestained samples by each tested detergent composition.

As shown from Table 3, overall detergency performance of Example 2-8 is at the same level of benchmark AEO7 and MAGE4. Noticeably, Examples 2-8 showed better detergent performance on cotton samples than polyesters, which is particularly suited for the current trend of cotton cloth preference.

Example 13

Etherification of Glycerol and Dodecanol with Sulfonated Polystyrene as Catalyst Two types of sulfonated polystyrene copolymers (PSt-co-PSSA and PSt-b-PSSNa/PSSA) were prepared as shown in Scheme 1. In the case of random copolymer, polystyrene (PSt) samples were synthesized in the lab following a standard ATRP procedure with 4-(bromomethyl) benzoic acid as initiator, copper chloride or bromide for the dormant/active species equilibrium and 2,2'-bipyridine to complex the copper. Two series of samples were made, with an average number molecular weight of 12500 g/mol and 26600 g/mol and a polydispersity index of 1.2. Random sulfonation of the samples was done by mixing PSt with the calculated amounts of acetic anhydride and sulfuric acid in 1,2-dicholoroethane to obtain polystyrene-co-polystyrene sulfonic acid (PSt-co-PSSA).

Blocked type ones (PSt-b-PSSNa/PSSA) were prepared through sequential polymerization through nitroxide mediated polymerization. Specifically, sodium polystyrene sulfonate (PSSNa) was prepared by nitroxide mediated polymerization with TEMPO and $K_2S_2O_8$+$Na_2S_2O_5$ in ethylene glycol:water of 3:1 weight. A polymer with 6500 g/mol average number molecular weight and a polydispersity index of 1.3 was obtained. The second block of polystyrene (PSt) was added in the same conditions. At the end, PSSNa-

TABLE 3

|  | Ex. 2 | Ex. 3 | Ex. 4 | Ex. 5 | Ex. 6 | Ex. 7 | Ex. 8 | AEO7 | MAGE4 |
| --- | --- | --- | --- | --- | --- | --- | --- | --- | --- |
| JB01 | 13.3 | 14.1 | 16.4 | 17.6 | 16.2 | 15.6 | 16.0 | 18.5 | 18.4 |
| JB02 | 5.42 | 6.73 | 6.94 | 7.17 | 7.06 | 7.04 | 6.08 | 5.66 | 6.52 |
| JB03 | 6.90 | 9.20 | 11.6 | 12.5 | 11.7 | 12.3 | 12.9 | 15.1 | 15.8 |
| CS61 | 32.3 | 22.9 | 23.0 | 23.4 | 23.1 | 22.6 | 24.6 | 27.2 | 25.7 |
| EMPA | 8.93 | 10.3 | 10.2 | 11.7 | 10.9 | 10.3 | 10.6 | 11.1 | 10.3 |
| Sum on cotton[1] | 66.8 | 63.2 | 68.1 | 72.4 | 69.0 | 67.7 | 70.2 | 77.5 | 76.6 |
| 20C | 0.34 | 0.25 | 1.48 | 2.29 | 1.53 | 1.32 | 2.35 | 5.10 | 3.39 |
| 20D | 4.92 | 3.94 | 8.20 | 8.28 | 7.77 | 7.77 | 9.30 | 13.7 | 9.83 |
| 20PF | 1.95 | 2.07 | 5.08 | 5.98 | 5.21 | 4.86 | 6.36 | 10.7 | 8.42 |
| Sum on PE&Cotton[1] | 7.20 | 6.26 | 14.8 | 16.6 | 14.5 | 14.0 | 18.0 | 29.5 | 21.6 |
| 30C | 2.44 | 6.64 | 16.5 | 16.7 | 16.1 | 15.0 | 17.1 | 19.8 | 18.6 |
| 30D | 1.10 | 1.34 | 10.1 | 12.3 | 9.44 | 8.87 | 9.48 | 17.9 | 13.9 |
| 30PF | 0.76 | 1.86 | 5.71 | 5.02 | 5.55 | 4.41 | 5.27 | 10.4 | 7.15 |
| Sum on PE[1] | 4.29 | 9.85 | 32.3 | 34.0 | 31.1 | 28.3 | 31.9 | 48.0 | 39.7 |
| AVERAGE[2] | 7.12 | 7.21 | 10.5 | 11.1 | 10.4 | 10.0 | 10.9 | 14.1 | 12.5 |

[1]The sum of stain removal rates for different cloth material
[2]The average stain removal rate for different stains and cloth material b-PSt was stirred with a cation exchange resin (previously conditioned with $H_2SO_4$, 4.2 eq/g) in water and tetrahydrofuran (THF) to yield a partially or fully protonated block polymer PSt-b-PSSNa/PSSA.

Scheme 1 Synthesis of Schemes of PSt-co-PSSA and PSt-b-PSSA

A) Synthesis of PSt-co-PSSA

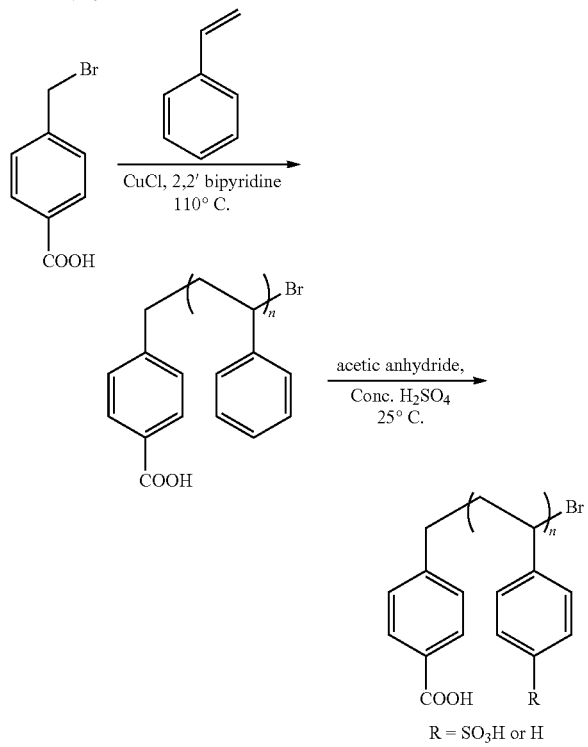

B) Synthesis of PSt-b-PSSA

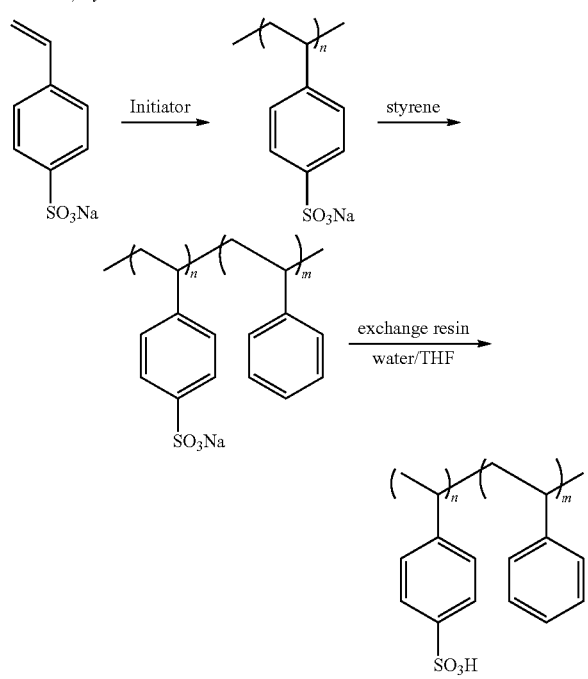

In a 250 mL two-neck round-bottomed flask fitted with magnetic stir bar and a water trap on one neck, dodecanol (24.1 g), glycerol (47.8 g) and a certain amount of sulfonated polystyrene (see Table 4) were added. The reaction mixture was vigorously stirred at 150° C. for 24 hrs. After the mixture cooled, pyridine was added to neutralize the catalyst. Optionally, the reaction was carried out with water removal (WR) under static vacuum. The obtained product composition was analysed by $^1$H NMR, GC-MS and HPLC, see Table 4.

TABLE 4

| Catalyst Sample[1] | Catalyst Quality[2] | Composition characterized by $^1$H NMR, GC and HPLC (wt %) | | | Dodecanol Conversion (%) |
| --- | --- | --- | --- | --- | --- |
| | | C12—OH (%) | C12-ether (%) | Ether product (%) | |
| $RC_{211}S_{21}$ | 0.1 | 21 | 35.9 | 43 | 79 |
| $RC_{211}S_{56}$-WR | 0.1 | 40 | 6.2 | 53 | 60 |
| $BC_{46}S_{50}$-WR | 0.05 | 32 | 10.8 | 57 | 68 |

[1]'R' represents random sulfonated polystyrene PSt-co-PSSA samples, 'B' represents blocked copolymer of PSt-b-PSSNa/PSSA samples, $C_x$ means that the number of styrene on the polystyrene chain is x, and $S_y$ means that the sulfonation degree of polystyrene is y %. 'WR' indicates that the reactions were done with water removal under static vacuum.
[2]Expressed as acidity eg. dodecanol Example 14

Etherification of Glycerol and Dodecanol with Sulfonated Polystyrene-Grafted Silica Particles as Catalyst Synthesis of silica nanoparticles grafted with PSt-co-PSSA was adapted from the general Scheme 2, except that $CuCl_2$ was also added together with CuCl to better control the polymerization of styrene in bulk. Silica ($SiO_2$) nanoparticles (10 g) were first stirred in 10% HCl for 1 hour, in a 3-neck round bottomed flask and at room temperature. After drying, 200 mL of dried toluene and initiator ((chloromethyl)phenylethyl) trimethoxysilane (CPMS, 16.7 ml, 67.9 mmol) were added to the 3-neck round bottom flask, under a nitrogen flow, and the mixture was refluxed for 4 hours, to have the CPMS initiator grafted on the particle surface. Styrene was grafted on the silica particle surface by ATRP (Atom Transfer Radical Polymerization) and using CuCl, $CuCl_2$ and 2,2'-bipyridine in a 50 mL Schlenk, and the polymerization was performed at 90° C. for 29 hours. The obtained PSt grafted silica nanoparticles were subsequently submitted to sulfonation under the same sulfonation condition for making random PSt-co-PSSA samples.

Three samples (Samples 1-3 in Table 5) with different sulfonation degree were thus prepared and related data are listed at Table 5. TGA measurements showed that the grafting degree on the nanoparticles is 5.9 wt %, and the consequent calculation showed that roughly 23% of silanol groups were connected to PSt chain, whose particle size and specific surface area remaining similar to parent silica particles. The sulfonation degrees of PSt were measured to vary from 42 to 90 mol % (calculated by TGA and titration methods), with acidity varying between 1.2 to 2.7 mmol/g (measured by titration).

Scheme 2 General procedure of PSt-co-PSSA grafting on silica nanoparticles

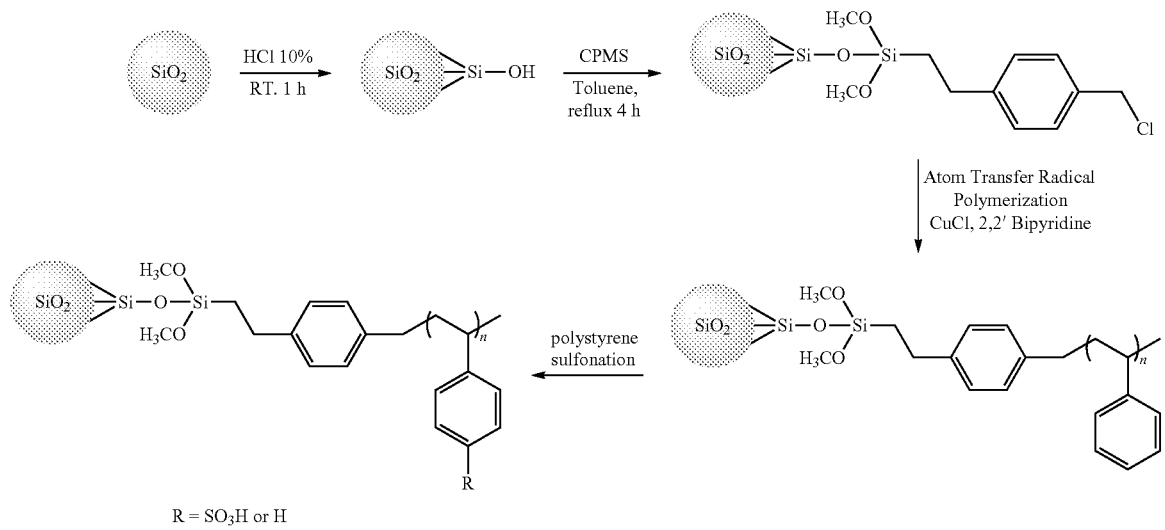

R = SO$_3$H or H

Next, in a 250 mL two-neck round-bottomed flask fitted with magnetic stir bar and a water trap on one neck, dodecanol (24.1 g) and glycerol (47.8 g) were added together with a grafted silica nanoparticle sample (Sample 1, 2 or 3, 0.05 H$^+$ eq. dodecanol). The reaction mixture was vigorously stirred at 150° C. for 24 hrs under static vacuum. After the mixture cooled, pyridine was added to neutralize the catalyst. Viscous product was obtained. The obtained product was characterized by $^1$H NMR and GC to get the average compositions which was listed in Table 5.

TABLE 5

| Grafted silica particle sample | Sulfonation Degree (molar %/PSt) | Acidity (mmol/g) | Composition characterized by $^1$H NMR, GC and HPLC (wt %) | | |
|---|---|---|---|---|---|
| | | | C12—OH (%) | C12-ether (%) | Ether product (%) |
| Sample 1 | 42 | 1.2 | 29 | 24.5 | 46 |
| Sample 2 | 59 | 1.8 | 39 | 13.4 | 48 |
| Sample 3 | 90 | 2.7 | 37 | 10.7 | 52 |

Recycling of Polymer Catalyst after the Etherification Reaction

Example 15

Recycling of Catalyst Nafion® NR50 for the Etherification of Triglycerol and Dodecanol In a 20 mL Schlenk tube fitted with an inside water trap, dodecanol (1.60 g), glycerol (3.16 g) and Nafion® NR50 (0.29 g, 3% eq. to dedecanol) were added. The reaction mixture was vigorously stirred at 150° C. under static vacuum until conversion of dodecanol was reached to be above 80% (verified by GC). Then, until the mixture was cooled and diluted with THF, the catalyst was collected by centrifuge. After washing with methanol and subsequent drying, the recovered catalyst was put in next cycle for the same etherification reaction as before. The conversion rate of dodecanol in the subsequent cycles was listed below in Table 6.

TABLE 6

| Cycle No. | Sampling time after the initial catalyst addition (hr) | Conversion of Dodecanol (%) | Selectivity of ether product (%) |
|---|---|---|---|
| 1 | 43 | 91 | 22 |
| 2 | 47 | 95 | 8 |
| 3 | 48 | 93 | 18 |
| 4 | 54 | 88 | 23 |

As seen from Table 6, the recycled polymer catalyst of Nafion® NR50 exhibited nearly unmodified catalytic behaviour when re-used in the same type of etherification reaction.

Example 16

Recycling of Aquivion® Catalyst for the Etherification of Triglycerol and Dodecanol In a 20 mL Schlenk tube fitted with an inside water trap, dodecanol (1.60 g), glycerol (3.16 g) and Aquivion® D66-20BSX (0.60 g, 6% eq. to dedecanol) were added. The reaction mixture was vigorously stirred at 150° C. under static vacuum until conversion of dodecanol reached 80% (measured by GC). Then, until the mixture was cooled and diluted with THF, the catalyst was collected by centrifuge. After washing with methanol and subsequent drying, the recovered catalyst was put in next cycle for the same etherification reaction as before. The conversion rate of dodecanol in the subsequent cycles was listed below in Table 7.

TABLE 7

| Cycle No. | Sampling time after the initial catalyst addition (hr) | Conversion of Dodecanol (%) | Selectivity of ether product (%) |
|---|---|---|---|
| 1 | 26.5 | 85 | 22 |
| 2 | 27.0 | 93 | 18 |
| 3 | 32.5 | 87 | 37 |

As seen from Table 7, the recycled polymer catalyst of Aquivion® D66-20BSX also exhibited nearly unmodified catalytic behaviour when re-used in the same type of etherification reaction.

The invention claimed is:

1. A process for preparing at least one ether compound, the process comprising reacting at least one alcohol (I) with at least one polyol (II) in the presence of a functional polymer [polymer (F)] as a catalyst (X), wherein:
the alcohol (I) is a compound represented by the general formula (1):

wherein $R_1$ is a hydrocarbon group having 1 to 36 carbon atoms, the polyol (II) is represented by the general formula (2):

wherein $R_2$ represents the skeleton moiety of the polyol and m is an integer of from 2 to 20,
and the polymer (F) is a polymer comprising recurring units derived from at least one ethylenically unsaturated monomer [monomer (M)] and bearing at least one cation exchange group;
wherein the reaction of the at least one alcohol (I) with the at least one polyol (II) in the presence of the functional polymer [polymer (F)] as the catalyst is performed in the absence of a solvent, and a medium for the reaction of the at least one alcohol (I) with the at least one polyol (II) in the presence of the functional polymer [polymer (F)] as the catalyst is substantially free of any surfactant at the start of the reaction.

2. The process of claim 1, wherein the at least one cation exchange group in the polymer (F) is selected from the group consisting of:
$SO_2X$, wherein X is halogen or $—O^-M^+$, wherein $M^+$ is a cation selected from the group consisting of $H^+$, $NH_4^+$, $K^+$, $Li^+$, $Na^+$, and mixtures thereof;
COY, wherein Y is halogen; $—O^-M^+$, wherein $M^+$ is a cation selected from the group consisting of $H^+$, $NH_4^+$, $K^+$, $Li^+$, and $Na^+$; $—OR_{Hy}$ wherein $R_{Hy}$ is a $C_1-C_6$ hydrocarbon group; $—OR_{Hf}$ wherein $R_{Hf}$ is a $C_1-C_6$ fluorocarbon or per(halo)fluorocarbon group; $—N(R_{Hy^*})_2$, wherein $R_{Hy^*}$, equal or different at each occurrence, is hydrogen or a $C_1-C_6$ hydrocarbon group, or mixtures thereof; and
$PO_2Z$, wherein Z is halogen; $—O^-M^+$, wherein $M^+$ is a cation selected from the group consisting of $H^+$, $NH_4^+$, $K^+$, $Li^+$, and $Na^+$; $—OR_{Hy}$, wherein $R_{Hy}$ is a $C_1-C_6$ hydrocarbon group, $—OR_{Hf}$ wherein $R_{Hf}$ is a $C_1-C_6$ fluorocarbon or per(halo)fluorocarbon group, or mixture thereof.

3. The process of claim 2, wherein each of X, Y and Z is independently $—O^-H^+$.

4. The process of claim 2, wherein the cation exchange group complies with formula $—SO_2X$.

5. The process of claim 2, wherein the polymer (F) comprises recurring units derived from styrene.

6. The process of claim 4, wherein the polymer (F) is selected from a group consisting of sulfonated styrene-divinylbenzene copolymers, sulfonated crosslinked styrene polymers, phenol-formaldehyde-sulfonic acid copolymers, and benzene-formaldehyde-sulfonic acid copolymers.

7. The process of claim 1, wherein the polymer (F) consists essentially of:
recurring units derived from one or more than one ethylenically unsaturated monomer comprising at least one fluorine atom and free from hydrogen atoms; and
recurring units derived from one or more than one ethylenically unsaturated monomer comprising at least one fluorine atom and at least one cation exchange group, and free from hydrogen atoms (except those optionally in the cation exchange group).

8. The process of claim 7, wherein the polymer (F) consists essentially of:
from 5 to 25% by moles of recurring units derived from (perfluoro-2-(2-fluorosulfonylethoxy)propylvinyl ether) (PSEPVE) and/or perfluoro-5-sulphonylfluoride-3-oxa-1-pentene (SFVE), in their $—SO_2F$ or $—SO_2X''$ form, wherein X'' is halogen or $—O^-M^+$, wherein $M^+$ is a cation selected from the group consisting of $H^+$, $NH_4^+$, $K^+$, $Li^+$, $Na^+$, or mixtures thereof; and
from 95 to 75% by moles of recurring units derived from tetrafluoroethylene (TFE).

9. The process of claim 1, wherein the polymer (F) is used as a supported catalyst (X).

10. The process of claim 1, wherein the polymer (F) is grafted to or supported on solid particles having a medium diameter between 2 and 200 nm.

11. The process of claim 9, wherein the polymer (F) comprises recurring units derived from styrene.

12. A surfactant composition [composition (S)] consisting of:
(i) more than one ether compound of formula (3) [ether (E1)],

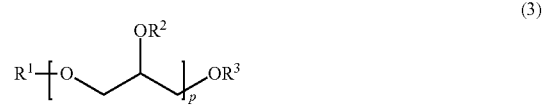

wherein: p is an integer from 1 to 36, and radicals $R^1$, $R^2$, and $R^3$, being same or different, are independently a hydrogen atom or a hydrocarbon group having 1 to 36 carbon atoms and optionally containing oxygen atom, provided that $R^2$ and $R^3$ are not hydrogen at the same time, and wherein $R^2$ optionally join together with $R^1$ or $R^3$ to form at least one oxygen-containing cyclic group having 3 to 7 carbon atoms;
(ii) at least one polyol (II) compound represented by the general formula (2):

wherein $R_2$ represents the skeleton moiety of the polyol and m is an integer of from 2 to 20; and,
(ii) optionally, at least one mono alkyl glyceryl ether (MAGE) compound of formula (4):

wherein a is an integer of from 1 to 20, and radical $R_1$ is a hydrocarbon group having 1 to 36 carbon atoms, wherein the ether (M1) components contain at least one ether compound of formula (5) [ether (E1-A)]:

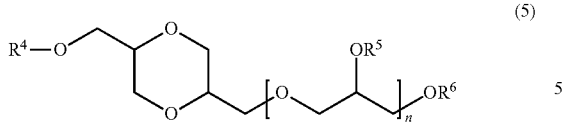

wherein: n is an integer from 0 to 36, and radicals $R^4$, $R^5$ and $R^6$, being same or different, are independently a hydrogen atom or a hydrocarbon group having 1 to 36 carbon atoms and optionally containing oxygen atom, wherein $R^5$ optionally join together with $R^4$ or $R^6$ to form at least one oxygen-containing cyclic group having 3 to 7 carbon atoms.

13. The process of claim 1, wherein the process comprises the following steps:
 a) mixing the at least one alcohol (I), the at least one polyol (II), and the catalyst (X);
 b) proceeding to the reaction of the ether compound by setting a temperature (T); and
 c) isolating the ether compound,
  wherein the ether compound includes at least one MAGE compound of formula (4)

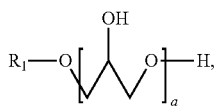

wherein a is an integer of from 1 to 20, and radical $R_1$ is a hydrocarbon group having 1 to 36 carbon atoms, and wherein the isolation step c) may be carried out according to the following steps:

c1) adding ethanol, water or mixture thereof into the reaction mixture obtained from step b);

c2) neutralizing the resultant solution of step c1) and filtering to obtain a filtrate;

c3) washing the filtrate obtained from step c2) with a polar solvent;

c4) concentrating the washed filtrate obtained from step c3) to obtain a concentrated liquid; and, c5) drying the concentrated liquid from step c4) and obtaining a crude MAGE compound.

14. The process of claim 2, wherein the halogen is Cl, F, Br, or I.

15. The process of claim 8, wherein $M^+$ is $H^+$.

16. The process of claim 10, wherein the solid particles having a medium diameter between 10 and 50 nm.

17. An application for home care or personal care comprising the composition (S) of claim 12.

\* \* \* \* \*